United States Patent [19]
De Ledinghen

[11] Patent Number: 5,929,635
[45] Date of Patent: Jul. 27, 1999

[54] DIGITAL OSCILLATOR AND SUPPLY CIRCUIT FOR AN EDDY CURRENT PROBE

[75] Inventor: Edouard De Ledinghen, Paris, France

[73] Assignee: Intercontrole, France

[21] Appl. No.: 08/930,178

[22] PCT Filed: Jun. 19, 1996

[86] PCT No.: PCT/FR96/00946

§ 371 Date: Oct. 20, 1997

§ 102(e) Date: Oct. 20, 1997

[87] PCT Pub. No.: WO97/01136

PCT Pub. Date: Jan. 9, 1997

[30] Foreign Application Priority Data

Jun. 20, 1995 [FR] France .................................. 95 07358

[51] Int. Cl.$^6$ .................................................. G01N 27/90
[52] U.S. Cl. ...................................... 324/236; 364/718.03

[58] Field of Search .................................... 324/236, 235, 324/239, 229, 230, 231, 232, 233, 234, 238; 364/718.03, 607; 327/107, 121

[56] References Cited

U.S. PATENT DOCUMENTS 4,283,768  8/1981  Scott .
4,529,936  7/1985  Rebour .

Primary Examiner—Jay M. Patidar
Attorney, Agent, or Firm—Burns, Doane, Swecker & Mathis LLP

[57] ABSTRACT

The present invention relates to a digital oscillator comprising an oscillator (40), a counter (41), a memory (42), a digital-analog converter (43) and a low-pass filter (44). The memory is able to directly store a complex signal, rendering the use of a real time calculating unit unnecessary.

3 Claims, 2 Drawing Sheets

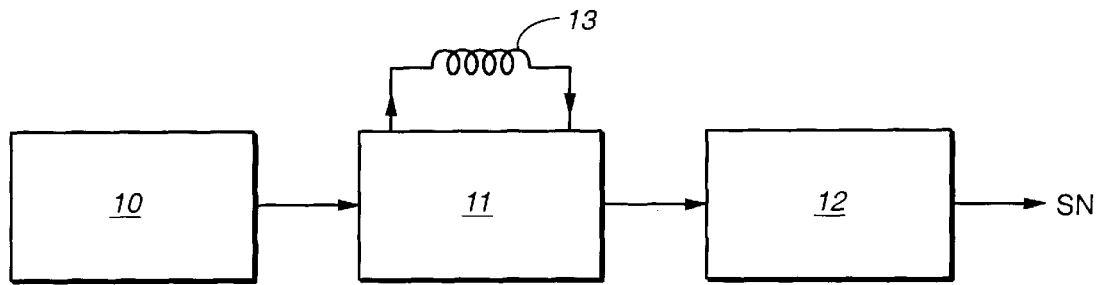
FIG._1
(PRIOR ART)
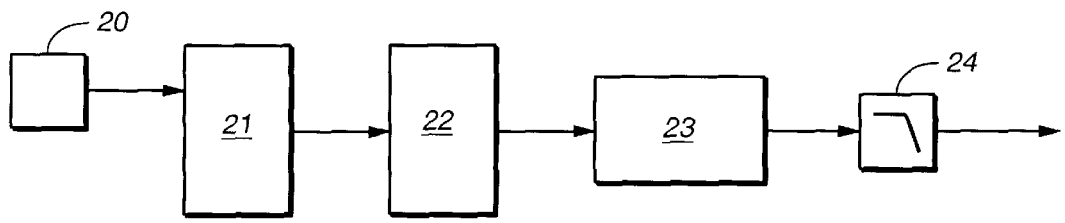
FIG._2
(PRIOR ART)
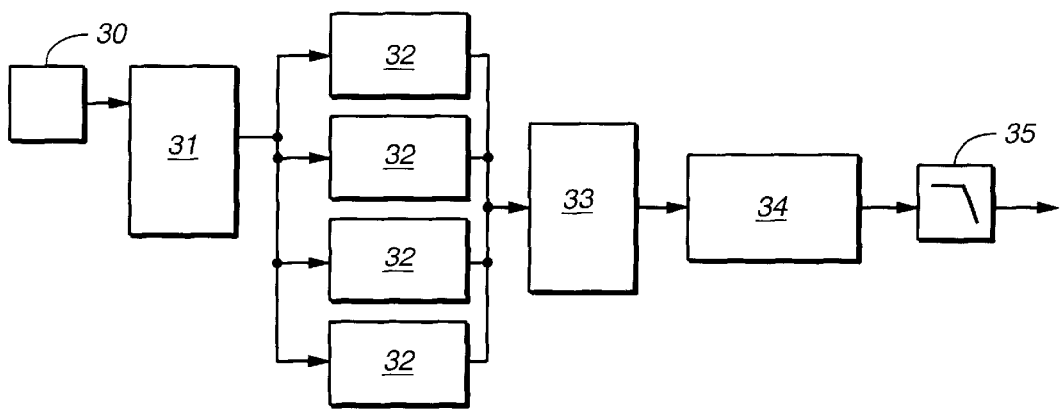
FIG._3
(PRIOR ART)

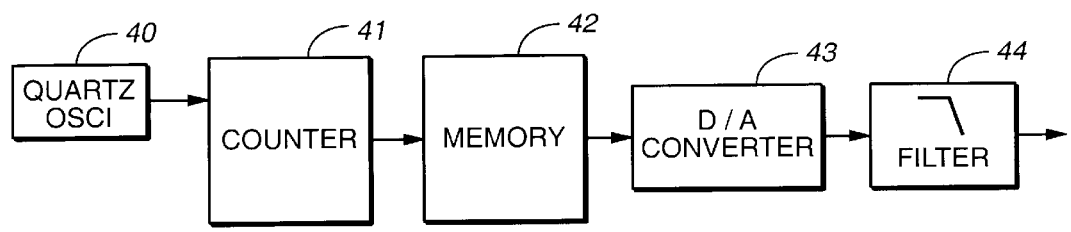
FIG._4
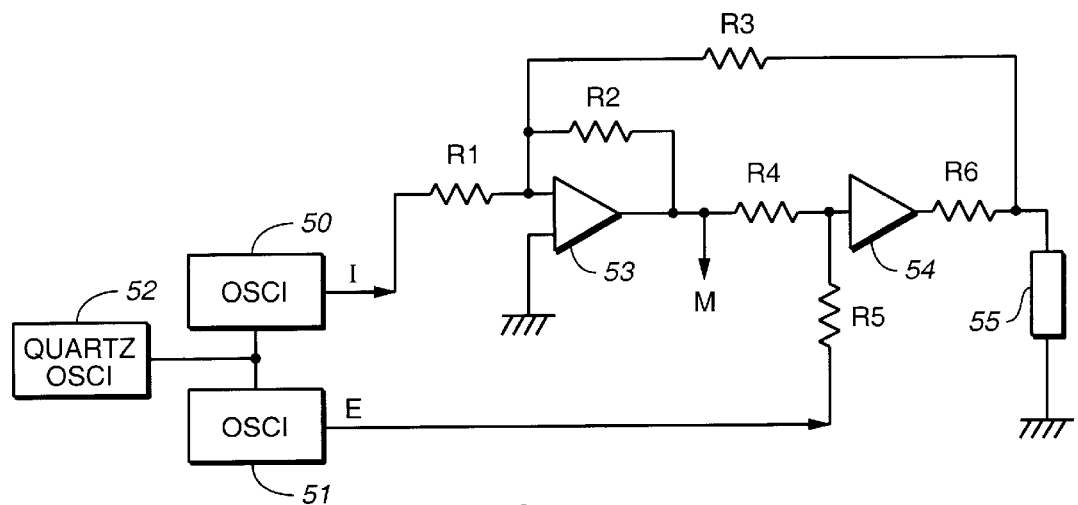
FIG._5

DIGITAL OSCILLATOR AND SUPPLY CIRCUIT FOR AN EDDY CURRENT PROBE

BACKGROUND OF THE INVENTION

1. Field of the Invention

The present invention relates to a digital oscillator and to a supply circuit for an eddy current probe.

2. State of the Art

A standard, multifrequency eddy current probe, as described in the work entitled "Non Destructive Testing Handbook" (MacMaster R. C. (ed), American society for Non Destructive Testing, 1986, vol. 4) and more particularly in sections 20 "Concepts of Multifrequency Eddy Current Testing" (R. Saglio, Intercontrole Inc., Rungis, France and M. Pigeon, Commissariat a l'Energie Atomique, France) and 11 "Electronic Analysis Circuits for Eddy Current Test" (E. J. Strauts, Magnaflux Corporation, Chicago, Ill., USA) has a mimic diagram like that shown in FIG. 1. It successively comprises a balancing oscillator 10, an injector 11, as well as a demodulator 12 supplying a digital output SN.

The function of the oscillator is to produce a multifrequency signal on the basis of a sum of 1 to N pure sinusoids. The balancing means serves to minimize the influence of carriers in order to amplify in relative manner the modulating signal (eddy current signal).

The injector 11 supplies a sensor 13 in which the modulation by eddy currents takes place. The function of the demodulator 12 is to extract the modulating signal (modulation by eddy currents) from the carriers used.

In such an apparatus, the technical data are generally as follows:

- the sinusoidal carriers have a frequency between 1 KHz and 4 MHZ,
- a measuring apparatus currently uses between one and four carriers simultaneously,
- the pass band of the eddy current signals does not exceed 1 KHz,
- the modulation by eddy currents is a complex modulation: amplitude and phase,
- the demodulator 12 has the function of extracting these two informations for each of the carriers and extracts in Cartesian form the modulated signal in the sensor having the following equation:

Xcos(wt)+Ysin(wt). (the demodulator extracting X and Y.)

One way of implementing the oscillator function involves oscillating an operational amplifier-based circuit. The generated frequency then depends on the values of the passive components connected around the integrated circuit. The advantage is that the frequency produced can be accurately regulated with the aid of a simple potentiometer. The disadvantages are that the frequency regulation is manual, the characteristics of the signal produced (frequency, amplitude, quality) are sensitive to measurement-external parameters, such as temperature and an oscillator card is required for each carrier to be generated.

This oscillator can be a digital oscillator, like that described in the work "Circuits intégrés et techniques numériques" by R. Delsol (Editions SUP'AERO, pp 282–286, cf. particularly fig. XIII-8) having the structure shown in FIG. 2. It then comprises a quartz oscillator 20, a counter 21, a PROM 22, a digital-analog converter 23 and a filter 24.

The quartz oscillator 20 ensures a very high stability of the frequency produced. The counter 21 is a programmable counter, whose outputs constitute the address bus of the PROM. The PROM 22 is a system of nonvolatile memories erasable by ultraviolet radiation and consequently reprogrammable. These memories contain samples of a certain number of sinusoids digitized at the frequency of the quartz oscillator. The converter 23 is a fast, 12 bit digital-analog converter, being followed by a low-pass filter 21 responsible for eliminating the frequency of the quartz oscillator.

This oscillator has the advantage of not deriving as a function of the temperature or other external events. However, it suffers from the following disadvantages:

- the choice of frequencies is limited, so that at a given time all the frequencies which can be generated are stored in the PROM, so that if the user requires a frequency not in the memory, he must stop the apparatus, remove the PROMs from the oscillator card and replace them by another set of circuits,
- it is necessary to have a system like that shown in FIG. 2 for each frequency to be generated and four systems are required for a standard, multifrequency eddy current apparatus,
- it is not possible to generate any random frequency, the possible frequencies being given by the formula:

$$F = \frac{P \cdot F_q}{N}$$

P is the number of periods of digitized sinusoids,
$F_q$ is the frequency of the quartz oscillator,
N is the number of digitized points,
P and N are integers.

Thus, it is possible to generate more low frequencies than high frequencies. The principle is to divide $F_q$ by an integer. The resolution is more precise when in the high values of N, giving e.g.: P=1: a single sinusoid period is described, $F_q$=10 MHZ, N=4 giving a frequency of 2.5 MHZ, whilst for N=5 it is 2 MHZ or 500 KHz variation for a single step. Conversely, for N=400 it is 25 kHz and for N=401, 24,938 Hz, i.e. a variation of only 62 Hz for a single step. It is impossible to generate frequencies between 2 and 2.5 MHZ. This limitation can be prejudicial in the case of the use conditions of an eddy current apparatus.

Another type of digital oscillator is shown in FIG. 3. It comprises a quartz oscillator 30, a counter 31 followed by four memories 32, an adder 33, a digital-analog converter 34 and a filter 35.

On this occasion the counter 31 controls four address buses. The memories 32 are of the volatile type. They are loaded by digitized sinusoids, as for the PROMs. For each clock stroke of the quartz oscillator 30 an addition takes place between the four data buses of the memories. The addition takes place by a real time calculation unit. The output of the oscillator is the same as in the previous case.

This oscillator has the advantage of being able to generate a sum of signals and of being reprogrammable by parametrizing. A microprocessor installed in the apparatus is able to recalculate the samples to be stored in the memories. However, it has the disadvantage of a cumbersome structure with a complex control of the different buses and the different programmable counters.

Another prior art document, U.S. Pat. No. 4,283,768, describes a digital signal generator making it possible to generate complex wave shapes of multiple frequencies and selected phases in the time range.

SUMMARY OF THE INVENTION

The present invention relates to a digital oscillator incorporating an oscillator, a counter, a memory, a digital-analog converter and a low-pass filter, characterized in that the memory is able to directly store a complex signal, in particular a sum of sinusoids at different frequencies as used in eddy current measurement apparatuses, so that a real time calculating unit is not necessary.

The oscillator can be used in an eddy current apparatus for exciting, balancing and demodulating functions.

Advantageously said circuit has an output connected to an absolute measurement input. The two functions of detection of eddy currents and supplying the probe are separate. This circuit incorporates two amplifiers, the first ensuring the control of the voltage and making it possible to sample at its output an absolute measurement voltage and the second ensuring the supply of the probe.

Advantageously, the input of the second amplifier is connected to a balancing input and balancing takes place across a digital oscillator particularly appropriate for fulfilling this function.

BRIEF DESCRIPTION OF THE DRAWINGS

The present invention may be further understood from the following written description in conjunction with the appended drawings. In the drawings:

FIG. 1 illustrates a known, multifrequency eddy current apparatus.

FIG. 2 illustrates a first prior art digital oscillator.

FIG. 3 illustrates a second prior art digital oscillator.

FIG. 4 illustrates the digital oscillator according to the invention.

FIG. 5 illustrates a balancing system using the oscillator according to the invention.

DETAILED DESCRIPTION OF THE PREFERRED EMBODIMENTS

The oscillator according to the invention shown in FIG. 4 incorporates a quartz oscillator 40, a counter 41, a volatile memory 42, a digital-analog converter 43 and a filter 44.

The counter 41 is no longer programmable and permanently scans all the addresses of the memory 42. The innovation consists of directly storing in the memory 42 a complex signal, which is the sum of several electric signals, which can be square, triangular or sinusoidal, e.g. a sum of sinusoids instead of performing successive additions. The possible frequencies are given by the formula:

$$F = \frac{k \cdot F_q}{\text{memory size}}$$

$$k = 1, 2, 3 \ldots$$

Thus, the smallest possible frequency is the division of $F_q$, the frequency of the quartz oscillator, by the size of the memory used. It is then possible to generate all the multiples of this frequency, so that the resolution of the memory 42 is constituted by $F_q$/memory size at $F_q/2$.

Moreover, as all the frequencies are described by the same number of memory locations, it is easy to form the sum of several sinusoids prior to entering in the memory.

Thus, this solution combines the advantages of great design simplicity, resolution of possible frequencies dependent on the memory size, but fixed and a capacity to generate sums of sinusoids (or a sum of signals).

The aforementioned oscillator can be used in an eddy current probe supply circuit and the structure is then that shown in FIG. 5.

Two oscillators 50 and 51 generate two synchronized signals I and E, said two oscillators using the same quartz 52. These two signals serve on the one hand (I) for the injection and on the other (E) for balancing. The injection voltage I on a first input of a first amplifier 53 across a resistor R1, the second input of said amplifier being earthed, the output being connected to the input of another amplifier 54 across a resistor R4, the balancing voltage E also being connected to said input across a resistor R5. The output of the second amplifier 54 is connected to the eddy current probe 55 across a resistor R6. A resistor R2 is positioned between the first input and the output of the first amplifier 53. A resistor R3 is placed between the first input of the first amplifier 53 and the probe 55.

In an embodiment, the resistors have the following values:

R1=R3=1 K ohm

R2=40 K ohm

R4=2 K ohm

R5≅650 ohm

R6≅300 ohm

This structure leads to a significant improvement to the balancing process described in European patent EP-A-86 158. Thus, the latter patent describes a supply circuit for an eddy current probe having two windings, two parallel supply channels connected to a probe by a cable, each channel having a reference winding, and a feedback resistance amplification circuit, where balancing takes place by an amplifier positioned in each channel.

Thus, the phase regulation or control takes place in a very precise manner in the invention by loading into the memory of each oscillator one signal phase-displaced with respect to the other. Moreover, the need to generate a balancing signal is linked with the use of an injector of the type described in European patent EP-A-86 158.

I claim:

1. Supply circuit of an eddy current probe, comprising two digital oscillators generating two synchronized signals, one used for injection and the other for balancing, the two digital oscillators coupled to the same quartz oscillator, each digital oscillator comprising a counter connected to the quartz oscillator, a memory coupled to the counter which stores a complex signal, a digital-analog converter coupled to the memory and a low-pass filter coupled to the converter, the synchronized injection signal being input into a first amplifier which functions to provide voltage control and make it possible to sample at its output an absolute measurement voltage corresponding to eddy currents, the output of said first amplifier being connected to an input of a second amplifier which functions to provide a supply voltage to the eddy current probe, the synchronized balancing signal being connected to said input of said second amplifier.

2. Circuit according to claim 1, characterized in that said output of said first amplifier is sampled so as to detect said absolute measurement voltage corresponding to said eddy currents.

3. Circuit according to claim 1, characterized in that the sampling of said absolute measurement voltage corresponding to said eddy currents and the supplying of the probe are performed separately.

* * * * *